United States Patent [19]

DeHaitre

[11] Patent Number: 4,701,165
[45] Date of Patent: Oct. 20, 1987

[54] REUSABLE SYRINGES

[75] Inventor: Lon DeHaitre, Arlington Heights, Ill.

[73] Assignee: Abbott Interfast Corp., Wheeling, Ill.

[21] Appl. No.: 844,141

[22] Filed: Mar. 26, 1986

[51] Int. Cl.$^4$ ............................................. A61M 5/315
[52] U.S. Cl. .................................................. 604/228
[58] Field of Search ............... 604/218, 222, 228, 232; 92/220, 209, 225, 214

[56] References Cited

U.S. PATENT DOCUMENTS

| 2,832,340 | 4/1958 | Dann et al. | 604/228 |
| 2,895,474 | 7/1959 | Rezner | 604/228 |
| 2,966,910 | 1/1961 | Camber | 604/228 |
| 4,215,701 | 8/1980 | Raitto | 604/222 |

Primary Examiner—John D. Yasko
Attorney, Agent, or Firm—Laff, Whitesel, Conte & Saret

[57] ABSTRACT

A reusable syringe has a push rod with a threaded entrance hole in its tip end. The threaded hole leads into an inner capture area. A shot package includes a glass tube with a plunger having a stud with an interrupted thread for passing through the thread entrance hole and becoming captured in the inner capture area. When the rod is pushed, the stud transfers forces to the plunger without applying compression forces thereto. This way, the plunger does not expand and chatter against the glass tube wall, thereby risking breaking it. The inventive stud with interrupted thread is otherwise identical to prior art studs which are fully threaded. Thus, the syringe may receive and is fully compatible with both types of studs.

21 Claims, 7 Drawing Figures

REUSABLE SYRINGES

This invention relates to syringes and, more particularly, to push rods for syringes, and especially for reusable syringes.

A syringe is a well known medical instrument for injecting medicines into or drawing blood from a patient's body. Insofar as the invention is concerned, a principal part is a shot package which includes a glass tube with a slidable plunger inside, which is used to push medicine out or to draw blood through a needle or cannula at the end of the glass tube.

The plunger is usually a soft, cylindrical rubber member which is pushed (or pulled) on the one of its sides which opposes the cannula. As the rubber plunger is pushed, it tends to expand and mushroom to seize the interior wall of the glass tube. A result is that the plunger tends to chatter as it slides along the tube. This chatter often causes the glass to break. The interior of the plug contains a bushing or threaded member which might tend to stress the plunger somewhat, as it is pushed, thereby tending to break a bond beween the bushing and the rubber.

A syringe with a new design should be usable with all existing shot packages, and a shot package with a new design should be usable with all existing syringes, since many devices are already present in the form of existing syringes, medicines (shots) already packaged in glass tubes, etc. Therefore, any solution to the problem of plunger chattering must provide a structure which is completely compatible with all existing equipment which is already in the field.

Accordingly, an object of the invention is to provide new and novel syringes. In this connection, an object is to provide tips for syringe push rods which prevent the expansion and mushrooming of the plunger, in order to avoid the kind of chattering which is likely to break a glass tube used in such a syringe or to rupture the bond between the plunger and the bushing to which it is anchored.

Another object of the invention is to provide a new and improved reusable syringe associated with disposable shots packaged in glass tubes which are preloaded with individual doses without any of the above-described failures. Here, an object is to provide such new syringes which are compatible with existing shots, and new shots which are compatible with existing syringes. A further object is to provide shots having rubber plungers which do not mushroom when pushed.

Yet another object of the invention is to provide syringes with individual and disposable glass tube and cannula assemblies which may be used to draw blood, and to draw blood, mix it with a medicine, and return the mixture to the same patient without any of the above-described failures.

Still another object is to provide for these and other objects in a low cost and economical manner.

In keeping with an aspect of the invention, these and other objects are accomplished by providing a unique connecting system between a syringe and a removable shot package which will prevent failure and which will be compatible with pre-existing systems that are already in the field. More particularly, the reusable syringe receives a shot package including a glass tube and cannula combination which may be inserted therein. The glass tube contains a sliding rubber plunger. The rubber plunger has a threaded stud or stem with an interrupted thread for providing an inner end including an undercut shank with a threaded outer end, which other end bottoms against an end wall in an associated clearance room or cavity in the push rod. Thus, overtorquing does not draw the push rod tightly against the plunger, which, in turn, prevents the plunger from expanding and mushrooming by being drawn too tightly against the end of the push rod. Also, the end of the stud has a bushing forming an anchor member which is molded into the rubber plunger. The bonding surface area between the bushing and plunger prevents a failure of the bond, such as the failures of the past which occur responsive to an overtorquing of the plunger against the end of the push rod.

A preferred embodiment of the invention is shown in the attached drawings, wherein.

Figure 1:
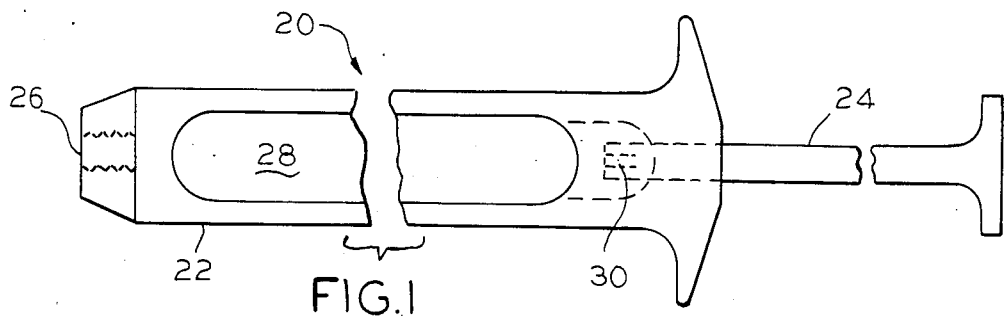
FIG. 1 is a plan view of an existing reusable prior art syringe, with which the invention should be compatible.

In FIG. 1, a reusable syringe 20 is shown in the form of an elongated housing or cylinder 22 with a push rod 24 on one end, an opening 26 on the other end for receiving a cannula or needle and a window 28 extending along the length thereof. The inner end of the push rod 24 has a tip end which contains a threaded hole 30 for receiving and capturing a threaded stud on a rubber plunger.

Figure 2:
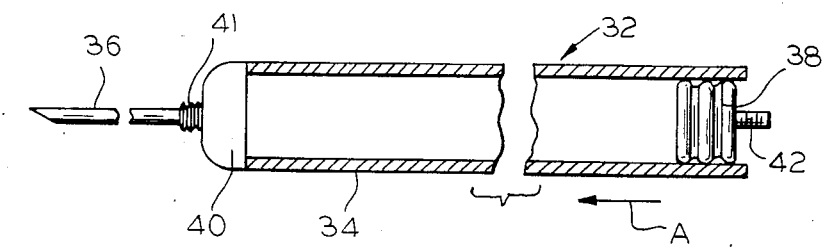
FIG. 2 shows a prior art shot package, partially in cross section, which may be used in both the prior art syringe of FIG. 1 and an inventive syringe.

The syringe 20 is used with individual shots (FIG. 2) which are packages in a disposable innoculation package 32 comprising a thin glass tube 34 having a cannula or needle 36 on one end and a sliding rubber plunger 38 inside the other end. The cannula 36 is held on the end of the glass tube 34 by a nose cap 40 having threads 41. The medicine is inside the glass tube 34, filling the space between the nose cap 40 and the plunger 38. When the plunger 38 is pushed in the direction A, the medicine is forced out of the cannula 36; or when pulled in an opposite direction, blood is drawn into the cannula. If the plunger is slid back and forth, blood may be drawn, mixed with a medicine, and returned to the patient. The plunger 38 is moved by a push rod 24 having an inner end with a hole which is threaded at 30 (FIG. 1) to receive the first and prior art type of fully threaded stem or stud 42 (FIG. 2) mounted on the rubber plunger 38.

In greater detail, the left-hand (as viewed in FIG. 2) end of shot package 32 is inserted into window 28 with the cannula base 41 threading into the opening 26. As the shot package 32 reaches its final resting position inside housing 20, the right-hand end of the glass tube passes into window 28 in the syringe, with the first type of threaded stem or stud 42 standing opposite and aligned with the threaded opening 30.

The push rod 24 is pressed against the end of the first type of threaded stud 42 and turned so that stud 42 enters into the opening 30. As the user continues to turn the push rod 24, the end of push rod 24 is cynched tightly against the rubber plunger 38. A continued application of a torque force pulls the thread stud 42 and, therefore, plunger 38 in direction B (FIG. 3), tightly against the end of the push rod, thereby causing a radial expansion of the plunger, as indicated by the arrows C, C. There is a mushrooming of the expanding plunger. When rod 24 is pulled or pushed, there is a tendency for the plunger to seize the interior wall of the glass tube. This causes a chattering of the plunger, as it moves, which may break the glass.

Also, the first type of threaded stud 42 ends in a knurled head bushing 50 about which and to which the rubber plunger is molded and bonded. As the torque is applied by turning the push rod 24, the threaded stud bushing 50 is turned within and is pulled away from the plunger. This turning and pulling tends to break the bond between the bushing 50 and the rubber plunger 38. This loss of bonding, can be particularly troublesome when the medical procedures requires the plunger to be pulled back, as when blood is drawn or to be pulled back and forth as when a small amount of blood is extracted, mixed with a medicine, and the mixture is returned to the blood stream.

Figure 4:
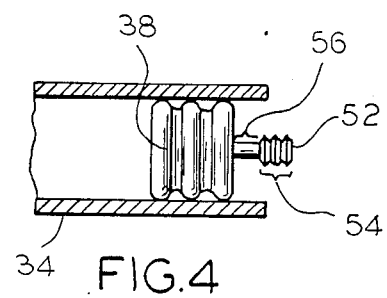
FIG. 4 is a side view of the inventive rubber plunger, showing an interrupted thread on a stud associated with the plunger.
Figure 5:
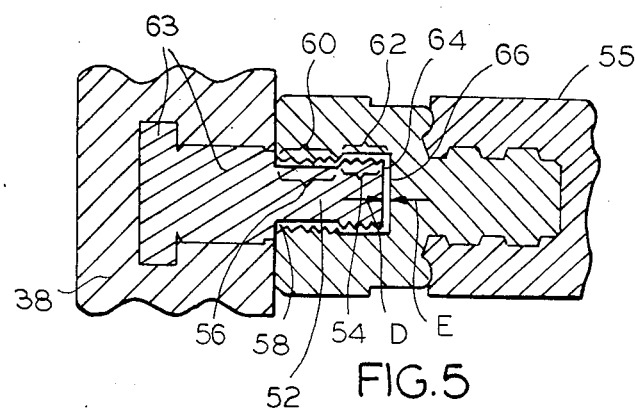
FIG. 5 is a cross section of the inventive end of the push rod and of the rubber plunger of FIG. 4, showing how the mushrooming of FIG. 3 is avoided.

The invention solves these and other problems as shown in FIGS. 4 and 5. The inventive plunger 38 has a second type of stud 52 with an interrupted thread, where the tip end 54 of the stud 52 is threaded while the inner end 56 of the stud is not threaded. Section 56 has a smooth periphery with a reduced diameter which slips freely through the threads at the entrance of the threaded hole 30, on the end of the push rod 24. Since the threaded end 54 of the second type of stud 52 has threads which match and mate with the threads in hole 30 of the prior art push rod 24, the inventive stud 52 is completely compatible with all pre-existing shots and syringes. Likewise, the inventive push rod tip (FIG. 6) may be used with all pre-existing shots or shot packages which are already in the field.

Figure 3:
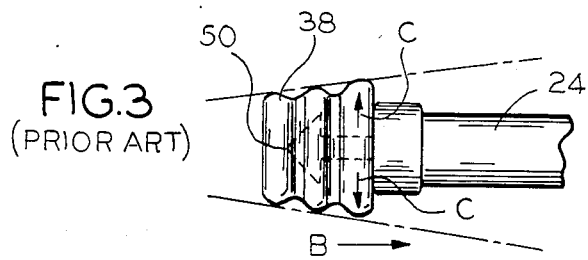
FIG. 3 is highly stylized and shows an exaggerated form of how the plunger of FIG. 2 may expand and mushroom to seize the interior wall of a glass tube.

The inner end of the inventive push rod 55 (FIGS. 5, 6) has a hole 58 with an initial or entrance section 60 having threads and a second and inner clearance room section 62 which is larger in diameter than the diameter of the threaded section 54 on the outer end of the second type and inventive stud 52. On the opposite end of the second type of stud 52 is a bushing 63 which has much more surface area as compared to the surface area of the prior art bushing 50 (FIG. 3). Thus, the bond between the inventive bushing and plunger is much more difficult to break than the prior art bond.

From an inspection of FIG. 5, it should now be apparent that, when the inventive push rod 55 is turned onto the end of the inventive stud 52, the two threaded sections 54 (on the stud) and 60 (in the hole) mesh and mate with each other. As torque continues to be applied by turning rod 55, the threaded section 54 on stud 52 enters the inner clearance room section 62. However, if the rod 55 is pulled without being turned, threaded sections 54, 60 interfere with each other and the stud 52 cannot leave the hole 58 responsive to pulling alone. Thus, the plunger is pulled back through the glass tube. Therefore, the stud 52 is captured at the end of the push rod so that the plunger and rod must move as a unit, longitudinally through the glass tube, although they may rotate freely with respect to each other.

It should be noted that, once end 54 enters the clearance room 62, no amount of continued turning of the push rod 55 will apply any additional pressure between the plunger 38 and the rod end. Thus, there are none of the forces represented by arrows B and C in FIG. 3. There is no expansion of the rubber plunger and no tendency for the non-expanded rubber plunger to seize the interior wall of the glass tube. Moreover, the stud 52 is not pulled deeper into the hole 58 to stress and, perhaps, break the bond between the bushing and rubber plunger.

When the push rod 55 (FIG. 5) is pushed, the end 64 of stud 52 bottoms against the end wall 66 of the inner clearance room 62. Thus, the forces which move the plunger are those represented by the arrows D and E in FIG. 5. Again, the external end of the push rod does not exert any compression forces on the plunger 38 so that there is none of the forces (arrow B, FIG. 3) which tend to expand the plunger 38 or to break the bond between bushing 63 and plunger 38. If the push rod 55 is pulled back, the larger threaded end 54 of stud 52 abuts against the entrance threads 60 so that the plunger 38 is also pulled back. However, since the push rod 55 is not turned, the plunger does not leave the end of the hole 58.

Figure 6:
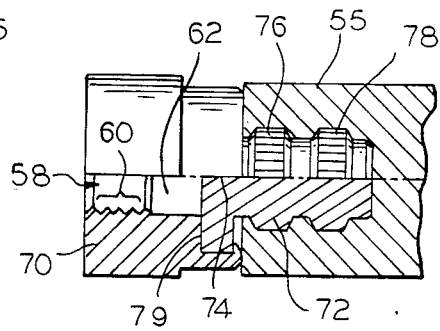
FIG. 6 is a cross sectional view of the end of the push rod which cooperates with the inventive stem.

FIG. 6 shows the actual construction of the tip end of the push rod 55 and hole 58 in the end of push rod 55. An end portion 70 (shown in half or partial cross section—i.e., below line 74) contains a hole 58 which is tapped in the entrance area 60. The opposite or inner end of the hole 58, has an enlarged area forming the inner clearance room 62. The anchor portion 72 is also shown, half in cross section (i.e., below line 74). Above the line 74, the exterior surfaces of both the end and anchor portions 70, 72 is shown in side elevation. Anchor portion 72 has two spaced parallel discs 76, 78, each with a serrated periphery to provide space for plastic to flow into as the push rod 55 is molded around it. The two portions 70, 72 may be a single part or the end portion 70 and the anchor portion 72 may be two separate parts which are bonded or welded or otherwise joined to each other, at their interfacing surfaces 79.

There are two methods of manufacturing the push rod with members 70, 72 therein. A first is by injection molding where plastic flows in and around the anchor portion. A second is where the push rod is molded with a hole having a contour that is complementary with the anchor portion. Then the anchor member is press fit in the hole, sometimes with cement or heat bonding.

It should now be apparent how the inventive parts interact and operate to prevent the rubber plunger 38 from being over-torqued and expanded. Thus, there is a far lesser chance for the plunger to chatter as it slides through the glass tube. There are little or no forces tending to break the bond between the bushing 63 and the rubber plunger 38. Moreover, the inventive push rod end 55 and plunger bushing and stud 52 are fully compatible with comparable and existing structures, shots, and the like.

A second embodiment uses an all metal syringe with the inventive tip end. The inventive rod tip can be fabricated as part of a metal push rod and processed to become a threaded hole with a clearance chamber or interrupted thread.

Figure 7:
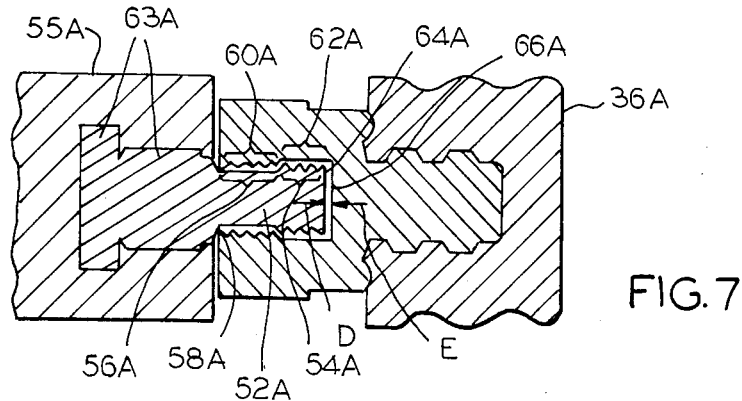
FIG. 7 is another embodiment with the stud and end assembly positions reversed.

A third embodiment (FIG. 7) represents a reversal of the unique connecting system wherein 52A has interrupted thread 54A on the end of the push rod 55A. The plunger 38 contains anchor portion 72A and end portion 70A.

Those who are skilled in the art will readily perceive how to modify the invention. Therefore, the appended claims are to be construed to cover all equivalent structures which fall within the true scope and spirit of the invention.

The claimed invention is:

1. A push rod for a syringe, said push rod having a hole in its end, a first section of the hole being threaded near the entrance of the hole, a second section of the hole which is remote from the entrance having an internal diameter which is larger than the diameter of the first threaded section in order to form a clearance room at the inner end of said hole, a plunger having a stud with an interrupted thread, the outer end of said stud having a thread which meshes and mates with the thread in said first section and the inner end of said stud having a smooth perimeter with a diameter which is less than the diameter of said first section of said hole, whereby said smooth inner end of said stud moves freely within the threaded section near the entrance of said hole.

2. The push rod of claim 1 wherein said stud has an end which is opposite its threaded outer end, a bushing formed on said opposite end of said stud, said bushing being bonded to said plunger.

3. The push rod of claim 2 wherein said bushing has a relatively large surface area to form a large bonding area between said bushing and plunger.

4. The push rod of claim 1 wherein the length of said stud is such that said threaded end of said stud bottoms on a wall of said inner clearance room when said rod is pushed, at which time the external end of said push rod does not exert compression forces on said plunger.

5. The push rod of claim 4 wherein said threads in said first section of said hole interfere with said threads on the outer end of said stud when said rod is pulled without being turned.

6. The push rod of claim 1 wherein said push rod is formed of molded plastic and a member having an end portion defining the hole at the end of said push rod and an anchor portion for providing points where said plastic forming said push rod may seize said anchor portion, said end portion and anchor portion being bonded to each other in order to form said member.

7. The push rod of claim 1 wherein there are two different types of studs, one type of said stud being fully threaded and having the same physical dimensions as the other type of said studs which is said stud with said interrupted thread, whereby both said fully threaded stud and said stud with interrupted threads may be used with the same push rod.

8. The push rod of claim 1 wherein said push rod is metal and said hole is formed at the end of said metal rod.

9. A reusable syringe comprising an elongated housing having a window therein for receiving a shot packaged in a tube with a plunger therein; a first type of shot package having a plunger with a fully threaded first stud projecting from an end thereof; a second type of shot package including a plunger with a second stud having an interrupted thread projecting from an end thereof, the threads on said second stud being at an outer end thereof; the fully threaded stud and the stud with an interrupted thread having the same length, diameter, and thread; a push rod extending through an end of said elongated housing, said push rod having a hole in an inner end thereof which confronts said stud in each of said types of said shot packages, said hole having a thread at the entrance thereof which mesh and mates with the threads on both the first and second studs of both types of said shot packages, and a clearance room at the inner end of said hole to receive the threads on the outer end of said second stud.

10. The syringe of claim 9 wherein the depth of said hole and the length of said stud are such that at least said second type of stud bottoms on an end wall of said hole when said rod is pushed, the length of said second stud being such that said plunger does not receive compression forces from said end of said push rod when said stud is bottomed in said hole.

11. The syringe of claim 9 wherein said push rod has an end portion integral with an anchor portion, said end portion containing said hole, said anchor portion having a peripheral configuration which locks into a surrounding plastic material, and said push rod comprises a plastic material which is conformed to said peripheral configuration.

12. The syringe of claim 11 wherein said end portion and said anchor portion are a single piece.

13. The syringe of claim 11 wherein said end portion and said anchor portion are two pieces which are integrally joined together.

14. The syringe of claim 11 wherein an opposite end of said stud has a bushing and said plunger is a soft rubber member molded around said bushing.

15. The syringe of claim 11 wherein said second stud with said interrupted thread has an outer threaded tip end and an inner section with a smooth periphery which slides freely through the threads at the entrance of said hole once said second stud is fully threaded into said hole.

16. A syringe comprising an elongated housing with a push rod at one end, means in said housing for receiving a shot package having a plunger with a stud projecting therefrom, means comprising a hole at the tip end of said push rod for receiving and capturing said stud, both said stud and said hole having approximately the same acceptable thread length whereby said syringe may accommodate standardized prepackaged shots, and means associated with said tip end and said stud for limiting compressive forces which may be applied between an end of said push rod and said plunger whereby said syringe may interchangeably accommodate both said standardized prepackaged shots and shots having said means for limiting said compressive forces.

17. The syringe of claim 16 wherein there are two types of said studs, one having a fully threaded length and the other having an interrupted thread, said two types of studs having the same length, diameter and thread whereby each may fit into and be captured within said hole.

18. A syringe comprising an elongated housing with a push rod at one end, means in said housing for receiving a shot package having a plunger with an end assembly having a threaded hole therein, means comprising a stud at the tip end of said push rod for receiving and capturing said end assembly, both said stud and said hole having approximately the same acceptable thread length whereby said syringe may accommodate standardized prepackaged shots, and means associated with said tip end and said end assembly for limiting compressive forces which may be applied between an end of said push rod and said plunger.

19. A push rod for a syringe, said push rod and an associated plunger having a mutual assembly system, said plunger having an end member with a hole in its end, a first section of the hole being threaded near the entrance of the hole, a second section of the hole which is remote from the entrance having an internal diameter which is larger than the diameter of the first threaded section in order to form a clearance room at the inner end of said hole, said push rod having a stud with an interrupted thread, the outer end of said stud having a thread which meshes and mates with the thread in said first section and the inner end of said stud having a smooth perimeter with a diameter which is less than the diameter of said first section of said hole, whereby said smooth inner end of said stud moves freely within the threaded section near the entrance of said hole.

20. The push rod of claim 1 wherein said end member has an anchor portion which is opposite said hole, a plunger formed on and bonded to said anchor portion of said end member.

21. A reusable syringe comprising an elongated housing having a window therein for receiving a shot packaged in a tube with a plunger therein; a push rod extending through an end of said elongated housing, the end of said push rod having a stud with an interrupted thread projecting therefrom; said plunger having an end member with a hole in an inner end thereof which confronts said stud on said push rod, said hole having a thread at the entrance thereof which mesh and mates with the threads on said stud at the end of said push rod, and a clearance room at the inner end of said hole to receive the threads on the outer end of said stud.

* * * * *